Figure 1:
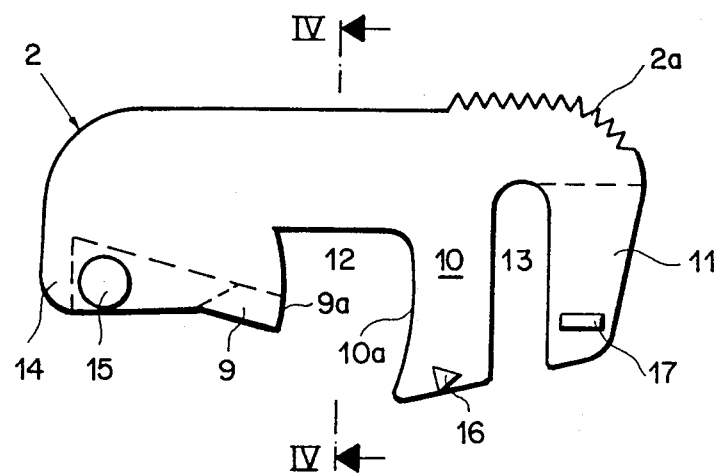

United States Patent [19]

Herrli

[11] Patent Number: 4,676,476
[45] Date of Patent: Jun. 30, 1987

[54] SHUT-OFF AND SEVERING DEVICE

[75] Inventor: Peter Herrli, Biel, Switzerland

[73] Assignee: Contempo Products, P. Herrli, Biel, Switzerland

[21] Appl. No.: 875,011

[22] Filed: Jun. 17, 1986

[30] Foreign Application Priority Data

Jun. 24, 1985 [CH] Switzerland .................. 2670/85

[51] Int. Cl.⁴ .................................................. F16K 7/06
[52] U.S. Cl. ........................................ 251/9; 30/134; 128/346
[58] Field of Search ............. 128/346; 30/131, 134; 137/1, 797; 251/9, 10; 604/34, 250

[56] References Cited

U.S. PATENT DOCUMENTS

| | | | |
|---|---|---|---|
| 3,125,108 | 3/1964 | Murphy | 137/68.1 |
| 3,323,208 | 6/1967 | Hurley | 30/134 X |
| 3,598,289 | 8/1971 | Norris | 222/80 |
| 3,822,052 | 7/1974 | Lange | 251/10 |
| 4,588,160 | 5/1986 | Flynn et al. | 128/346 X |
| 4,589,626 | 5/1986 | Kurtz et al. | 128/346 X |

Primary Examiner—Gerald A. Michalsky
Attorney, Agent, or Firm—Zarley, McKee, Thomte, Voorhees & Sease

[57] ABSTRACT

The device consists of a first part having two parallel walls and a second part hinged to the first part. The first part is provided with four coaxial pairs of catch openings and the second part with three coaxial pairs of projections. Upon swivelling of the second part between the walls of the first part, the pairs of projections snap successively into the corresponding pairs of catch openings, whereby the tube previously inserted in the first part is clamped and subsequently cut through. By making it possible to clamp and sever the tube with a single device, greater security is ensured for the patient.

7 Claims, 8 Drawing Figures

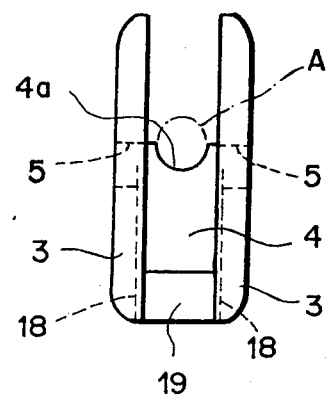
FIG. 3
FIG. 4
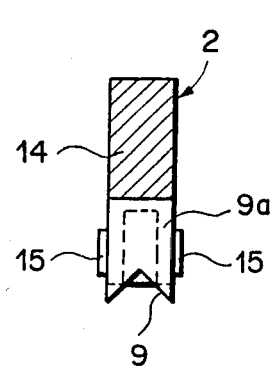
FIG. 5
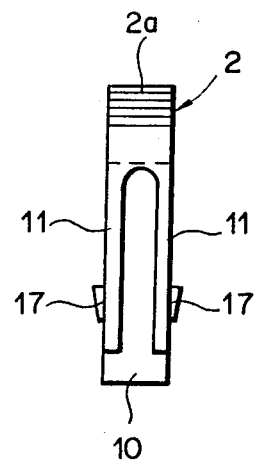

SHUT-OFF AND SEVERING DEVICE

This invention relates to devices for controlling the flow of fluids through tubing, and more particularly to a two-part device for shutting off and severing a resilient tube such as is used in home dialysis, for withdrawal of blood, or for intravenous injection, of the type in which the tube has been placed in a first part of the device, and to a method of operating the device.

This method and device are used, for example, in peritoneal dialysis. In ambulatory dialysate exchange, the patient need not wear any bag of fresh or used dialysate on his or her body. A catheter is introduced into the patient's abdominal cavity and attached to a connecting piece of resilient tubing. The end of a Y-tube connected to the bag of fresh dialysate and to the bag of used dialysate is attached to the connecting piece by means of metal connectors. After the used dialysate has been drained off from the patient's abdomen into the waste bag, the Y-tube must be closed and then severed. The closure is achieved by clamping, whereby bacteria are supposed to be kept from entering the patient's abdomen, and scissors are used for severing the tube.

The separate closure and severing operations have heretofore been carried out in five steps which the patient has had to learn. However, bacterial infection of the peritoneum has always been a frequent occurance nonetheless.

U.S. Pat. No. 3,822,052 describes a manually operated clamping device for controlling the flow of fluid through flexible tubing. The device consist of a strip of plastic which can be bent to form a base and an overlying lever arm, each having an abutment. The abutments are disposed opposite one another so that the inserted tubing can be clamped between them. The clamping action is achieved by snapping the lever arm into an upright portion of the strip. By swivelling the upright portion, the lever arm can be released from it and the tube thus unclamped.

This device can be used only for clamping the tube and is not provided with any means for severing it (cutting it through).

It is an object of this invention to provide an improved method and device for shutting off and severing a tube through which liquid flows, providing greater security for the patient than heretofore in that no open tube results after severance, which has always represented a danger to the life of the patient.

It is further object of this invention to provide a device enabling even an untaught patient to shut off and sever a tube by hand without effort, wherein the individual positions of the course of movement are audible.

Another object of the invention is to provide a device which eliminates the several operations carried out in the past, as well as ensuring that the tube is not cut off on the wrong side.

Still another object of this invention is to provide a shutting off and severing device which is inexpensive to manufacture.

To this end, in the two-part device according to the present invention, of the type initially mentioned, the first part has two parallel walls between which a cradle piece for the tube is accommodated, four coaxial pairs of catch openings being provided in the walls, the second part has a mounting arm with a cutting edge, a clamping nose, and two catch springs, the cutting edge being separated from the clamping nose by a first gap, and the clamping nose being separated from the catch springs by a second gap, and three coaxial pairs of projections being provided on each side of the second part, the second part being pivotably secured to the first part by means of its first pair of projections provided on the mounting arm and snapped into the first pair of catch openings, and being snappable during the course of its pivoting movement into the second pair of catch openings by means of the second pair of projections provided on the clamping nose and successively into the third and fourth pairs of catch openings by means of the third pair of projections provided on the catch springs.

In this method of shutting off and severing a tube according to the present invention, the tube is first clamped and thereafter cut through at a distance from the clamping location in a single movement, running along an arcuate line, of the othr part of the two-part device, pivotably secured to the first part.

Figure 2:
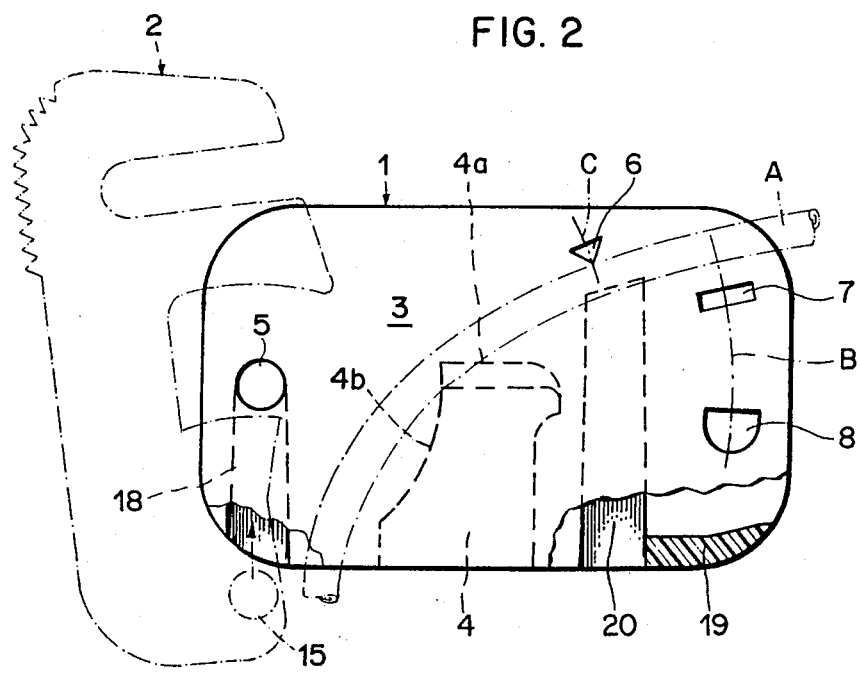
Figure 6:
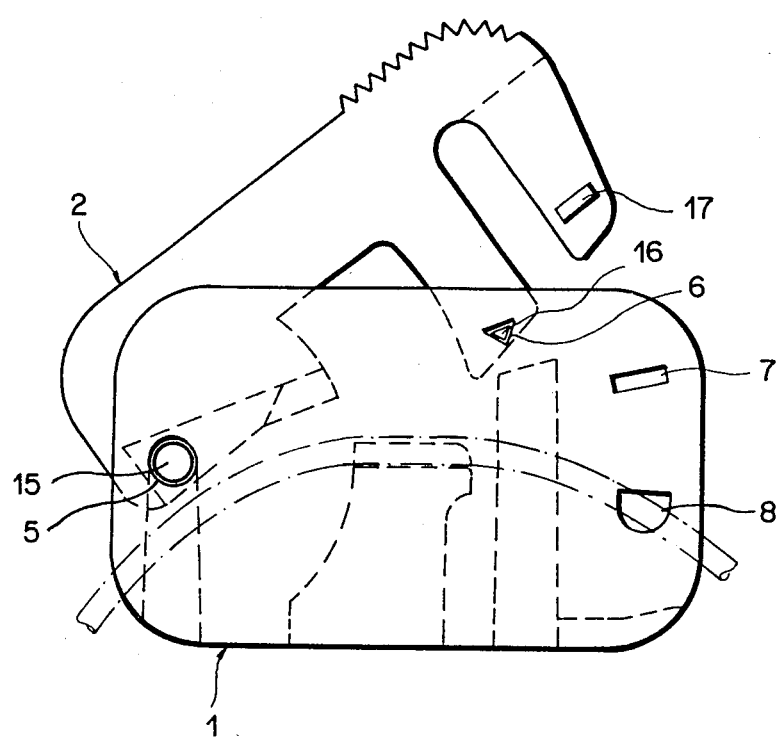
Figure 7:
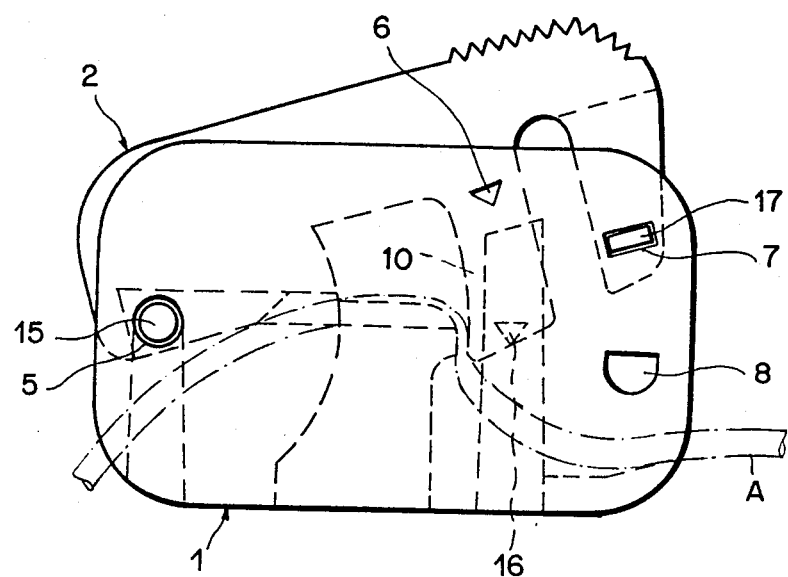
Figure 8:
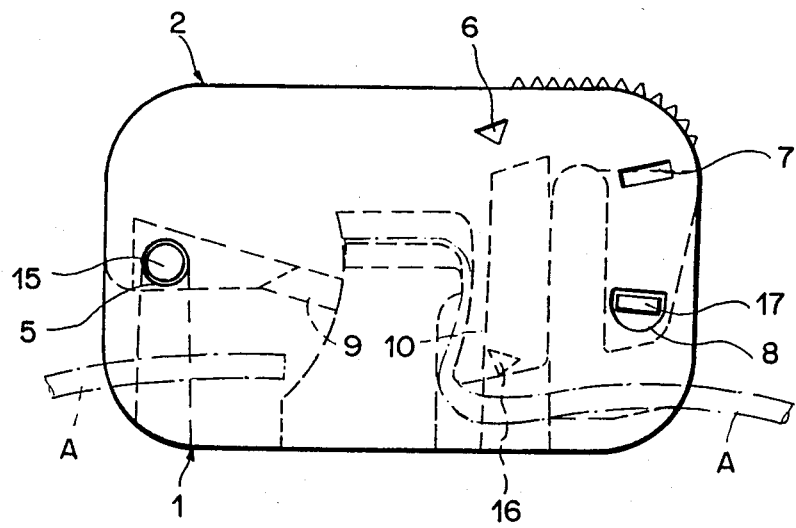

A preferred embodiment of the invention will now be described in detail with reference to the accompanying drawings, in which:

FIG. 1 is an elevation of one part of the device, which part can be hinged to the other part shown in FIG. 2, FIG. 2 is an elevation of the other part of the device, FIG. 3 is an end-on view of the other part according to FIG. 2, FIG. 4 is a section taken on the line IV—IV of FIG. 1, FIG. 5 is an end-on view of the springs according to FIG. 1, and FIGS. 6, 7, and 8 are elevations of the device assembled from the two parts in various snap-in positions.

A first part 1 of the two-part device illustrated in FIG. 2 has two parallel, rectangular walls 3, between which a cradle piece 4 is accommodated. The cradle piece 4 forms part of one of the long sides of the first part 1, on the one hand, and extends to about halfway up the wall, on the other hand, so that there is formed on the other long side of the part 1 between the walls 3 a slot for inserting a resilient tube A for carrying a liquid. A tube-guiding groove 4a provided in the cradle piece 4 is used for positioning the tube A. The first part 1 further comprises a reinforcing plate 19, as well as four coaxial pairs of catch openings 5, 6, 7, 8 in the two walls 3.

The second part 2 illustrated in FIG. 1 has a mounting arm 14 with a cutting edge 9, a clamping nose 10, and two catch springs 11. Between the cutting edge 9 and the clamping nose 10 there is a first gap 12, and between the clamping nose 10 and the catch springs 11 there is a second gap 13. On each side of the second part 2 there are three coaxial pairs of projections 15, 16, and 17. The first pair of projections 15 is on the mounting arm 14, the second pair 16 on the clamping nose 10, and the third pair 17 on the springs 11.

Before the first pair of projections 15 is slid through entry grooves 18 and snapped into the first pair of catch openings 5 in the first part 1, the tube A is laid in the guiding groove 4a of the cradle piece 4 in such a way (see FIG. 3) that it rests against a surface 4b of the cradle piece 4 facing the first pair of catch openings 5. When the first pair of projections 15 has been snapped into the first pair of catch openings 5, the second part 2 is hinged to the first part 1. The path of movement of the hinged second part 2 is arcuate. The arc followed by the second pair of projections 16 is designated as C in FIG. 2, while the arc followed by the third pair of projections 17 is designated as B.

In the course of its swivel movement, the second pair of projections 16 on the clamping nose 10 snaps into the second pair of catch openings 6, and the third pair of projections 17 on the catch springs 11 snaps successively into the third and fourth pairs of catch openings 7 and 8. In the first snap-in position 5, 15, the device is in "flow" position, i.e., the liquid can flow unhindered through the tube A. The device is supplied to the patient in this first snap-in position together with the tube and the bags. In the second snap-in position 7, 17, the tube A is pressed by the clamping nose 10 against the cradle piece 4 in Z shape and completely shut-off so that no medium (liquid or air) can pass through this clamping location. Between the second snap-in position 7, 17 and the third 8, 17, the tube A is cut through by the cutting edge 9. When the projections 16, 17 snap into the catch openings 6, 7, 8, a clearly audible click is heard.

The cutting edge 9 takes the form of an angled blade. The cutting surface 9a facing the first gap 12 is arcuate and corresponds to the arcuate shape of the cradle piece surface 4b facing the first pair of catch openings 5. By this means, the tube A is cut off transversely at a distance from the clamping location.

The clamping nose 10 by which the tube A is shut-off is made of solid material. For this reason, it cannot yield laterally like the springs 11. The second pair of projections 16 is therefore guided in grooves 20 on the inside surfaces of the walls 3. The surface 10a of the clamping nose 10 facing the first gap 12 is likewise arcuate, whereby the tube A is clamped even more firmly.

In order to be able to distinguish better visually as well among the individual pairs of catch openings 5, 6, 7, 8, and the pairs of projections 15, 16, 17 corresponding thereto, they are designed in differing geometric shapes and colors. Thus, the first pair of catch openings 5 is circular, the second pair of catch openings 6 triangular, the third pair of catch openings 7 rectangular, and the fourth pair of catch openings 8 semicircular. The associated pairs of projections have matching shapes. As may be seen in FIG. 5, the pair of projections 17 on the springs 11 is shaped in such a way that after it has snapped into the catch openings 7, there is no possibility of any reopening, i.e., any swivelling back of the second part 2. The same naturally applies to the snap-in position 8, 17. These two snap-in positions ensure double security for the patient.

The device is composed of only two parts made of hard plastic by injection molding. It is flat, at most 3×5 cm in size and 1 cm thick. A device of this form can be comfortably worn by the patient on his or her body. A grooved portion 2a on the edge of the second part 2 remote from the second gap 13 facilitates movement of that part with the thumb.

Both operations, viz., clamping and subsequent severing of the tube, are carried out by a single device as described above. This device is designed in such a way that the tube need not be pulled through it but is placed lengthwise in the guiding groove of the cradle piece. Because it is disposable, the device cannot be reused. Being made in two parts, it is economical to manufacture, and as it requires no tools, it is easy to assemble.

What is claimed is:

1. A device for shutting off and severing a tube, comprising
    a first part having
        two parallel walls,
        a cradle piece disposed between said walls for accommodating said tube, and
        first, second, third, and fourth coaxial pairs of catch openings in said walls, and
    a second part having
        a mounting arm including a cutting edge,
        a clamping nose separated from said cutting edge by a frist gap,
        two catch springs separated from said clamping nose by a second gap,
        a first pair of coaxial projections disposed on said mounting arm and snappable into said first pair of catch openings for pivotably securing said second part to said first part,
        a second pair of coaxial projections disposed on said clamping nose and snappable into said second pair of catch openings, and
        a third pair of coaxial projections disposed on said catch springs and snappable into said third and fourth pairs of catch openings.

2. The device of claim 1, wherein said mounting arm further includes an arcuate cutting surface facing said first gap, said cradle piece including an arcuate surface facing said first pair of catch openings and matching said arcuate cutting surface.

3. The device of claim 1, wherein said cutting edge takes the form of an angled blade.

4. The device of claim 1, wherein said clamping nose includes an arcuate surface facing said first gap.

5. The device of claim 1, wherein the edge surface of said second part remote from said second gap is grooved.

6. The device of claim 1, wherein said pairs of catch openings and said pairs of projections are of differing geometrical shapes.

7. The device of claim 1 made of hard plastic and having a flat shape at most 1 cm thick, 5 cm long, and 3 cm wide.

* * * * *